(12) United States Patent
Matsuura

(10) Patent No.: US 8,586,021 B2
(45) Date of Patent: Nov. 19, 2013

(54) ARTIFICIAL TERMITE EGG HAVING β-GLUCOSIDASE AS TERMITE EGG RECOGNITION PHEROMONE, AND CONTROL OF TERMITES USING THE SAME

(75) Inventor: Kenji Matsuura, Okayama (JP)

(73) Assignee: National University Corporation Okayama University, Okayama (JP)

( * ) Notice: Subject to any disclaimer, the term of this patent is extended or adjusted under 35 U.S.C. 154(b) by 235 days.

(21) Appl. No.: 12/995,752

(22) PCT Filed: Jun. 1, 2009

(86) PCT No.: PCT/JP2009/059982
§ 371 (c)(1),
(2), (4) Date: Jan. 3, 2011

(87) PCT Pub. No.: WO2009/148017
PCT Pub. Date: Dec. 10, 2009

(65) Prior Publication Data
US 2011/0091409 A1    Apr. 21, 2011

(30) Foreign Application Priority Data

Jun. 2, 2008   (JP) ................................ 2008-144663

(51) Int. Cl.
*A01N 25/00* (2006.01)
*A01M 1/20* (2006.01)
*C12N 9/14* (2006.01)
*C12N 9/36* (2006.01)
*C12N 9/42* (2006.01)

(52) U.S. Cl.
USPC ............ 424/84; 43/132.1; 435/195; 435/206; 435/209

(58) Field of Classification Search
USPC ............. 424/84; 43/132.1; 435/195, 206, 209
See application file for complete search history.

(56) References Cited

U.S. PATENT DOCUMENTS

2010/0028323 A1    2/2010 Matsuura et al.

FOREIGN PATENT DOCUMENTS

| JP | 2000-342149 | 12/2000 |
| JP | 2008-194007 | 8/2006 |
| JP | 4258785 | 2/2009 |

OTHER PUBLICATIONS

Matsuura et al., Cuckoo fungus mimics termite eggs by producing the cellulose-digesting enzyme b-glucosidase. Current Biol., 2009, vol. 19: 30-36.*
Weil et al., Molecular basis for the reproductive division of labour in lower termite. BMC Genomics, 2007, vol. 8:198, pp. 1-9.*
English translation of the International Preliminary Report on Patentability dated Jun. 15, 2010.
K. Matsuura et al., "The Antibacterial Protein Lysozyme Identified as the Termite Egg Recognition Pheromone", PLoS One, vol. 2, No. 8, pp. 1-16, 2007.
K. Sugio et al., "Koushun Shiroari ni Okeru Caste-kan-cellulase Kassei no Sai to Kyosei Gensei Dobutsu Jokyo no Eikyo", Japanese Journal of Applied Entomology and Zoology, vol. 50, No. 1, pp. 1-6, 2000.
"Termites and Strategies of Extermination", The Japan Termite Control Association, pp. 218-220, 2000 (with English translation).
T. Yoshimura et al., "Activity Evaluation of Japanese Undergound Termites using Monitoring Station and their Control with Bait Method", New Developments of Monitoring Technique of Insect Ecology in a Living Zone, pp. 48-53, 2006 (with English translation).

* cited by examiner

*Primary Examiner* — Ganapathirama Raghu
(74) *Attorney, Agent, or Firm* — Wenderoth, Lind & Ponack, L.L.P.

(57) ABSTRACT

The present invention provides a mimetic egg comprising β-glucosidase, a salt thereof, a biological fragment thereof or a β-glucosidase-related peptide as an egg recognition pheromone in its base material mimicking an egg of a insect pests, particularly a termite, a method for exterminating and controlling insect pests, and a tool for a biological study using the same.

5 Claims, 1 Drawing Sheet

ARTIFICIAL TERMITE EGG HAVING β-GLUCOSIDASE AS TERMITE EGG RECOGNITION PHEROMONE, AND CONTROL OF TERMITES USING THE SAME

This application is a U.S. national stage of International Application No. PCT/JP2009/059982 filed Jun. 1, 2009.

TECHNICAL FIELD

The present invention relates to a novel mimetic egg for exterminating and controlling insect pests, particularly a termite; and a method for exterminating and controlling insect pests, particularly a termite, and a tool for a biological study, using the same. More particularly, the present invention relates to a mimetic egg of a termite using β-glucosidase, a salt thereof, a biological fragment thereof or a related peptide thereof; and a method for exterminating and controlling a termite, and a tool for a biological study, using the same.

BACKGROUND ART

Damage due to insect pests is a severe problem in the world and various control methods have been developed so far. In particular, a termite among insect pests causes enormous damage to wooden houses, and therefore an extermination agent and an extermination method of a termite have been intensively researched and developed.

The method for exterminating a termite includes a method of injecting a solution agent such as an organophosphorus agent, a carbamate agent or a pyrethroid agent into an invasion place to kill an insect, or a method of performing smoking by methyl bromide or the like to kill an insect (see, for example, Non-patent Document 1).

As an alternative to a method of spraying an agent, there is a bait method in which a slow-acting insecticidal active ingredient is mixed in a bait and the bait is fed to a termite thereby exterminating the termite (see, for example, Non-patent Document 2).

The conventional extermination technique is basically to throw an agent in large quantity from the outside of a damaged wood to kill an insect. However the technique leads to health damage such as sick house syndrome or to environmental pollution. Moreover, there is a problem that if some of colonies of termites remain, the damage is made to spread to another place. The most serious problem is that the labor cost required for the extermination is too much. The fumigation technique using methyl bromide have been frequently carried out, however, methyl bromide is a causative substance of the ozone layer destruction, and in recent years, a tendency to try to regulate the use of methyl bromide has increased.

As a method for exterminating an ant which organizes a social life in the same manner as in a termite, there is an effective method of mixing a favorite food of an ant into a poison and providing the mixed food as a bait to allow the ant to bring the food to its nest and killing the entire population of the ant. However, because a termite eats the wood itself in which the nest is built, the bait method for allowing the termite to convey an agent from the outside of the nest to the inside of the nest by using a poison bait is not always effective. In particular, it is difficult to eradicate the nest of a termite that belongs to the genus *Reticulitermes* by the bait method (see, Non-patent Document 2).

As a method for making insect pests to ingest an active ingredient more efficiently than the bait method, "a method for exterminating insect pests by conveyance of a mimetic egg" has been developed in which an egg conveyance instinct that is a basic social behavior of insect pests is utilized (Patent document 1). A main ingredient of egg recognition pheromone is an antimicrobial protein called lysozyme and it has become apparent that lysozyme alone has an egg recognition pheromone activity (see Non-patent Document 3). It is also known that the addition of cellulase (EC3.2.1.4), i.e., endo-1,4-β-glucanase as an auxiliary substance of the termite egg recognition pheromone has the effect of enhancing a conveyance activity of a mimetic egg (see Patent Document 2, Non-patent Document 3).

Heretofore, there has been a method in which cellulase (EC3.2.1.4) is added to lysozyme as an auxiliary substance for stabilizing a conveyance activity of a mimetic egg. However, the conveyance activity is not remarkably improved by cellulase (Patent Document 2, Non-patent Document 3), and the egg conveyance activity which is equal to or more than that of an extract of the true termite egg has not been obtained yet.

Patent Document 1: Japanese Unexamined Patent Publication No. 2000-342149
Patent Document 2: Japanese Patent Application No. 2007-035030
Non-patent Document 1: "Termites and strategies for control", The Japan Termite Control Association, 2000, p. 219
Non-patent Document 2: "Activity evaluation of Japanese underground termites using a monitoring station and the control by bait methods", New developments of monitoring technique of insect ecology in a living zone, 2006, p. 48
Non-patent Document 3: Matsuura, K., Tamura, T. Kobayashi, N., Yashiro, T. Tatsumi, S.: The antibacterial protein lysozyme identified as the termite egg recognition pheromone. PLoS ONE 2(8): e813. doi:10.1371/journal.pone.0000813

DISCLOSURE OF INVENTION

Problems to be Solved by the Invention

An object of the present invention was to provide a mimetic egg, particularly a mimetic egg of a termite, which has a higher conveyance activity than that of a conventional one, and also to provide an exterminating and controlling method with more satisfactory efficiency, and a tool for a biological study.

Means for Solving the Problems

Under the above circumstances, the present inventors have intensively studied about a possibility of the involvement of a substance other than lysozyme, serving as termite egg recognition pheromone, in egg recognition so as to further improve and stabilize a conveyance activity of a mimetic egg. They have cyclopaedically investigated about a protein having a possibility of being produced by a termite itself and performed an egg conveyance activity test with respect to various protein preparations. As a result, they have succeeded in remarkably enhancing a conveyance activity of a mimetic egg by making a mimetic egg to contain β-glucosidase (EC3.2.1.21) known as a digestive enzyme of a termite, and thus completed present invention.

Therefore, the present invention provides the following:
(1) A mimetic egg comprising β-glucosidase, a salt thereof, a biological fragment thereof or a β-glucosidase-related peptide as an egg recognition pheromone in its base material mimicking an egg of a termite;

(2) The mimetic egg according to (1), wherein the base material comprises lysozyme, a salt thereof, a biological fragment thereof or a lysozyme-related peptide;
(3) The mimetic egg according to (1) or (2), wherein the base material comprises an ingredient extracted from an egg of a termite;
(4) The mimetic egg according to any one of (1) to (3), wherein the base material comprises cellulase, a salt thereof, a biological fragment thereof or a cellulase-related peptide;
(5) The mimetic egg according to any one of (1) to (4), wherein the base material comprises glycerol;
(6) The mimetic egg according to any one of (1) to (5), wherein the base material comprises lysozyme, a salt thereof, a biological fragment thereof or a lysozyme-related peptide, and cellulase, a salt thereof, a biological fragment thereof or a cellulase-related peptide;
(7) The mimetic egg according to any one of claims (1) to (6), comprising one or more ingredients selected from the group consisting of an insecticidal active ingredient, a hatch-inhibiting substance, a reproduction-inhibiting substance, a growth-inhibiting active ingredient, or insect pathogenic microbes;
(8) A method for exterminating a termite, which comprises providing the mimetic egg according to (7) to a termite; and making the termite to convey the mimetic egg into its nest utilizing an egg conveyance behavior; and
(9) A tool for a biological study essentially comprising the mimetic egg according to any one of (1) to (7).

Effects of the Invention

According to the present invention, the present inventors have succeeded in remarkably enhancing a conveyance activity of a mimetic egg by adding β-glucosidase as egg recognition pheromone of an insect, particularly a termite. The conveyance activity of a mimetic egg of the present invention was higher than that of an extract of the true termite egg (data after 48 hours, see Example). According to the present invention, it is possible to effectively exterminate and control insect pests by making insect pests, particularly a termite, to convey the mimetic egg, which contains an insecticidal active ingredient therein, into its nest utilizing an egg conveyance instinct of insect pests, particularly a termite. Also, the mimetic egg of the present invention can simply induce and observe an egg conveyance behavior of an insect, and therefore the mimetic egg is also suited as a tool for a biological study for learning and studying about a behavior and pheromone of an insect.

BEST MODE FOR CARRYING OUT THE INVENTION

Figure 1:
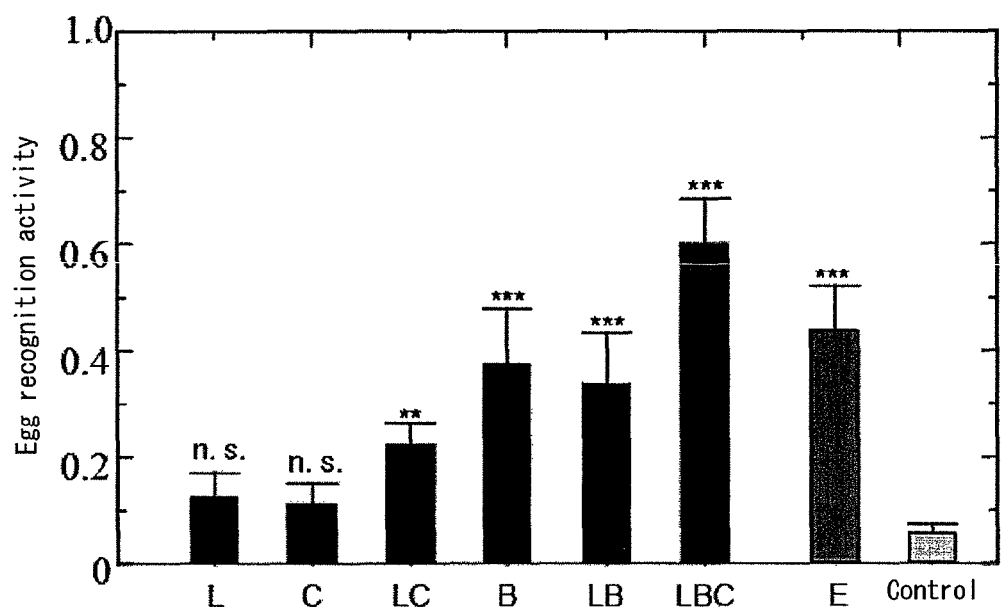
FIG. 1 shows results of investigation of an egg recognition activity (conveyance ratio) after 24 hours since initiation of a test. Each of abbreviations indicates as follows; L: egg white lysozyme, C: cellulase, LC: mixed solution of egg white lysozyme and cellulase, B: β-glucosidase., LB: mixed solution of egg white lysozyme and β-glucosidase, LBC: mixed solution of egg white lysozyme, β-glucosidase and cellulase, E: termite egg extract. n.s.: no significant difference from the control. : there is a significant difference with a significant level of 1%. *: there is a significant difference with a significant level of 0.1% (two-sided T test). An error bar in the drawing indicates a standard error.

Insects, such as a termite, which have a characteristic of conveying an egg have characteristics of taking care of an egg by conveying and stacking the egg in their nests and licking the surface of the egg and so forth, or performing a trophallaxis with other individual. By utilizing such characteristics, insect pests can be exterminated or controlled. For example, a termite recognizes a mimetic egg having a size and a shape similar to the natural egg, and containing egg recognition pheromone on the surfaces thereof, as an egg, and conveys the mimetic egg into its egg mass in the nest. In the nest, the termite performs a care behavior such as licking the surface of the mimetic egg and performs a trophallaxis with other individuals. Accordingly, reproduction center of colonies can be destroyed efficiently by making the mimetic egg contain an active substance, for example, an active ingredient such as an insecticidal active ingredient, a hatch-inhibiting substance, a reproduction-inhibiting substance, or a growth-inhibiting ingredient, and making the termite to convey the mimetic egg into the egg mass.

As described above, the present inventors have studied about a possibility of the involvement of a substance other than lysozyme, serving as egg recognition pheromone, in egg recognition so as to further improve and stabilize a conveyance activity of a mimetic egg. As a result, they have succeeded in remarkably enhancing a conveyance activity of a mimetic egg by adding β-glucosidase (EC3.2.1.21) known as a digestive enzyme of a termite, biological fragment thereof or a related peptide thereof, and thus completed the present invention. In other words, in the present invention, β-glucosidase known only as a digestive enzyme of a termite, a salt thereof, a biological fragment thereof or a related peptide were first used as egg recognition pheromone, and thus satisfactory results have been obtained.

Therefore, in a first aspect, the present invention provides a mimetic egg comprising β-glucosidase, a salt thereof, a biological fragment thereof or a β-glucosidase-related peptide as an egg recognition pheromone in its base material mimicking an egg of a termite.

The insect pests that convey the mimetic eggs of the present invention and can be exterminated by the method of the present invention, may be any insect pests as long as it has an egg conveyance instinct and recognizes β-glucosidase, a salt thereof, a biological fragment thereof or a β-glucosidase-related peptide as egg recognition pheromone. The insect pests to which the mimetic egg and the method of the present invention are preferably applied is a termite. The termite exterminated by the present invention may be any kind of termites, and termites not only in Japan but also in the world can be targeted. Typical examples of a termite exterminated by the present invention includes, but are not limited to, termites that belong to the genus *Reticulitermes* and the genus *Coptotermes*. In the present specification, extermination of insect pests also includes control of insect pests. In the present specification, insect pests means insects causing harmful effects on human, farm animals, farm products, assets, and so forth. Typical examples thereof include a termite.

In the present invention, β-glucosidase, a salt thereof, a biological fragment thereof or a related peptide is used as egg recognition pheromone. β-Glucosidase is widely distributed in microorganisms, plants and animals. The β-glucosidase used in the present invention may be derived from any kind, and examples of origins thereof include, but are not limited to, plants such as almond and cycad; animals such as termite, wood feeding cockroach, and snail; and microorganisms such as *Aspergillus oryzae*, yeast, Enterococcal, and bacterium belonging to genus *Bacillus*. The β-glucosidase used in the present invention may not be purified or may be purified. Furthermore, the β-glucosidase used in the present invention may be produced by a genetic recombination method. The production of protein, polypeptide, or peptide by a genetic recombination method is well known to those skilled in the art. In general, the desired protein can be obtained by connecting the gene of a desired protein to a vector and introducing it into an appropriate host cell such as *Escherichia coli* or yeast, and proliferating the cell. The kind of the vector or the host cell, a vector introduction condition, the culture condition of the host cell, a method of separating and purifying the desired protein, and so forth can be appropriately selected from known materials and known methods by those skilled in the art.

The β-glucosidase used in the present invention may be a form of a salt. The β-glucosidase salt may be a salt with every substance that can form a salt, for example, a salt with an organic acid, a salt with an inorganic acid, a salt with an organic base, or a salt with an inorganic base. Moreover, for example, a β- or γ-carboxyl group of asparagine acid or glutamine acid constituting the β-glucosidase and a metal such as sodium or potassium may form a salt. Moreover, for example, a salt may be formed with a side chain of a basic amino acid constituting the β-glucosidase. In the present invention, a biological fragment of β-glucosidase or a β-glucosidase-related peptide may have a form of a salt.

Furthermore, in the present invention, the biological fragment of β-glucosidase may be used as egg recognition pheromone. The biological fragment of β-glucosidase is a polypeptide or a peptide having a partial amino acid sequence of β-glucosidase and having a similar egg recognition activity to β-glucosidase. The fragment is a short chain, and is therefore suitable for large-scale production by a genetic recombination method.

Furthermore, in the present invention, the β-glucosidase-related peptide may be used as egg recognition pheromone. The β-glucosidase-related peptide is a protein, a polypeptide, or a peptide having a similar egg recognition activity to β-glucosidase and being different from β-glucosidase and the biological fragment of β-glucosidase. The β-glucosidase-related peptide may be derived from a natural source or may be a synthetic compound. The β-glucosidase-related peptide may have an amino acid sequence different from the natural β-glucosidase by a technique such as a site-directed mutagenesis method. For example, β-glucosidase, a biological fragment of β-glucosidase, or a β-glucosidase-related peptide having an amino acid sequence that is more favored by a termite may be produced and used in the present invention. Moreover, for example, β-glucosidase, a biological fragment of β-glucosidase, or a β-glucosidase-related peptide having an amino acid sequence having a high specificity to a specific termite may be produced and used in the present invention.

The content of β-glucosidase, a biological fragment of β-glucosidase or β-glucosidase-related peptide in the base material can be determined depending on various factors such as the kind, the characteristic, and the amount of the β-glucosidase to be used, the kind of the insect pests, the kind and the amount of an activity substance, and the kind and the extent of the desired effect.

The mimetic egg of the present invention has to have a shape, a size, and characteristics analogous to the shape, size, and characteristics of the egg of the insect pests to be exterminated. The form and size of the mimetic egg used in the present invention can be produced by mimicking the form and size of the natural egg of the insect pests. In the case of a termite, the form of the mimetic egg can be a long-egg shape or a spherical shape. In the case of the mimetic termite egg having a long-egg shape, it is preferable that its short diameter be approximately the same as or slightly larger than the short diameter of the egg of a termite to be exterminated. For example, when the short diameter of the termite egg is from about 0.25 to about 0.45 mm, the short diameter of the long-egg-shaped mimetic egg may be from about 0.25 to about 0.6 mm, preferably from about 0.4 to about 0.55 mm, and more preferably from about 0.45 mm. Moreover, in the case of the sphere-shaped mimetic termite egg, it is preferable that its diameter be approximately the same as or slightly larger than the short diameter of the egg of a termite to be exterminated. For example, when the short diameter of the termite egg is from about 0.25 to about 0.45 mm, the diameter of the spherical mimetic egg may be from about 0.25 to about 0.6 mm, preferably from about 0.4 to about 0.6 mm, and more preferably from about 0.45 to about 0.55 mm. From the viewpoint of easy formation, the spherical mimetic egg is preferable.

It is necessary that not only the physical property such as shape and size as described above and weight or hardness but also the chemical property, particularly the existing state of the egg recognition pheromone of the mimetic egg of the present invention be the same as or similar to those of the natural egg of the insect pests. That is, it is preferred that when the base material of the mimetic egg contains β-glucosidase, a biological fragment of β-glucosidase, or a β-glucosidase-related peptide, these substances appear on the surface of the base material.

The base material of the mimetic egg of the present invention may be any material which can produce the mimetic egg having a similar shape and characteristics to those of the natural egg of the insect pests. The base material preferable for the production of the mimetic egg of the present invention includes thermoplastic resins such as polyethylene, polypropylene, polystyrene, polyester, polyvinyl chloride and polycarbonate; thermosetting resins such as a urea resin, an epoxy resin, a phenol resin and polyurethane; and porous materials such as silica gel and zeolite; ceramics and glass.

The base material contains β-glucosidase, a salt thereof, a biological fragment thereof or a β-glucosidase-related peptide, and an active ingredient, thereby producing the mimetic egg of the present invention. Many methods for making these substances contained in the base material are known to those skilled person in the art. In the production of the base material, these substances may be mixed therein, or after producing the base material, these substances may be allowed to be contained in the base material. For example, in the production of the base material, these substances may be mixed or kneaded therein, or the produced base material may be covered, immersed, coated, or splayed with these substances. Moreover, because methods for immobilizing a protein, a polypeptide, or a peptide to a solid support are known, these methods may be applied thereto. The immobilizing method includes an adsorption method, a covalent bond method, an ionic bond method, an encapsulation method or the like.

The amount of β-glucosidase, a salt thereof, a biological fragment thereof or a β-glucosidase-related peptide applied to the base material of the mimetic egg of the present invention can be easily determined by those skilled in the art depending on various factors such as species (source organism), physicochemical property or the like, a kind of the insect pests, a kind or amount of the active substance, and a kind or degree of the desired effect (see, for example, Examples of the present application).

Preferably specific examples of the mode of making the base material to contain β-glucosidase, a salt thereof, a biological fragment thereof or a β-glucosidase-related peptide, and an active ingredient include a surface-coating mode, a base material addition mode, and a capsule dissolution mode. In an example of the surface-coating mode, an active ingredient is coated on the surface of a base material, and β-glucosidase, a salt thereof, a biological fragment thereof or a β-glucosidase-related peptide is coated thereon. In an example of the base material addition mode, on the surface of a base material in which an active ingredient is mixed, β-glucosidase, a salt thereof, a biological fragment thereof or a β-glucosidase-related peptide is coated. In an example of the capsule dissolution mode, a film-shaped base material is formed into a capsule shape base material, and an active ingredient is sealed therein, and β-glucosidase, a salt thereof, a biological fragment thereof, or a β-glucosidase-related peptide is coated on the surface of the base material.

The active substance that can be used for the mimetic egg and the extermination method of the present invention may be any substance which can accomplish extermination or control of insect pests. For example, the active substance may disturb the behavior of the insect pests, thereby leading to destruction of the colony. The active substance suitable for exterminating or controlling insect pests includes an insecticidal active ingredient, a hatch-inhibiting substance, a reproduction-inhibiting substance or a growth-inhibiting ingredient. A Kind and an amount of the active substance that can be used for the mimetic egg and the method of the present invention can be selected depending on various factors such as the kind of the active substance or the kind of the insect pests and the kind or the degree of the desired activity (damage to be given to the insect pests). In general, the kind and the amount of the active substance are selected so that the desired effect can be sufficiently exerted to the desired insect pests. However, the selection is also taken in consideration so that the conveyance rate of the mimetic egg of the insect pests will not be decreased, and so that the adverse effect to humans and circumjacent farm animals or beneficial insects will not be produced using the mimetic egg and the method of the present invention.

One kind of, or two or more kinds of the active ingredients may be used for the mimetic egg and the extermination method of the present invention. For example, the insecticidal active ingredients such as a pyrethroid compound, an organophosphorus compound, a carbamate compound, an N-aryldiazole compound, a hydrazone compound, a sulfonamide compound or natural insecticidal ingredients can be used. Additionally, insect growth regulators such as a chitin synthetic inhibitor, a juvenile hormone-like active compound, and a molting hormone-like active compound can be used as active ingredients. It goes without saying that the active ingredient that can be used in the present invention is not limited to the above compounds.

In the mimetic egg of the present invention, the active ingredient is preferably slow-acting. As described above, a insect pests such as a termite recognizes as an egg the mimetic egg having a size and a shape similar to the natural egg which contains an egg recognition pheromone on the surface thereof, and conveys the mimetic egg into its egg mass in the nest. A insect pests ingests the active ingredient through care behaviors such as licking the surface of the mimetic egg. When some individuals of the colony ingest the active ingredient, the active ingredient pervades the entire colony through a high-frequent trophallaxis by stomodeal food and proctodeal food. Accordingly, the preferable active ingredient used in the present invention does not exert the effect at the time of conveying the mimetic egg or immediately after ingestion by a insect pests, or exerts the effect at an extent of not affecting behaviors such as the mimetic egg conveyance or a trophallaxis, and exerts the effect after the mimetic egg is conveyed into the nest and the trophallaxis is performed among many individuals. By using such a slow-acting active ingredient, many individuals in the targeted colony can be efficiently exterminated, and the usage amount of the active ingredient is small. Accordingly, an influence on other ecological systems is also small. The slow-acting active ingredient that can be used for the mimetic egg of the present invention includes not only a slow-acting insecticidal ingredient such as hydramethylnon but also a slow-acting hatch-inhibiting ingredient, a slow-acting reproduction-inhibiting ingredient, and a slow-acting growth-inhibiting ingredient, but not limited thereto.

In the mimetic egg of the present invention, it is also preferable that the base material be made of a sustained-release material. The mimetic egg whose base material is made of a sustained-release material are preferable, whereby, the mimetic egg is conveyed into the nest and then the active substance is gradually released and taken in by the insect pests. Such a mimetic egg includes an egg made of a material that can be degraded by saliva of the insect pests. Preferably, the active ingredient is allowed to be contained inside the base material (by interfusion, blend, filling, or the like), the mimetic egg is conveyed into the nest and then the base material is degraded by saliva of the insect pests, and thus the inside active ingredient is released. In particular, in the case of the above base material addition mode or the capsule dissolution mode or the like, it is preferable to use the base material that can be degraded by saliva of the insect pests. The material of the base material that can be degraded by saliva of the insect pests can be selected depending on a kind of the digestive enzyme in the saliva of the insect pests. For example, when cellulase is contained in the saliva of the insect pests, the base material made of a cellulosic material can be used.

The particularly preferable type of the mimetic egg of the present invention is the above-mentioned capsule dissolution type. Specifically, the mimetic egg of the present invention can be produced by forming a film-shaped base material containing β-glucosidase, a salt thereof, a biological fragment of β-glucosidase or a β-glucosidase-related peptide into a shape similar to an natural egg (that is, to be a capsule form), and allowing the active ingredient to be contained inside the capsule. The method of forming such a capsule is known to those skilled in the art. Examples of the material of the film include an oxide film and a cellulose film. The film-shaped base material preferably has a sustained-release property, and it is preferable to use, for example, a cellulose film that can be degraded by saliva of the insect pests. The mimetic egg produced by such a capsule sealing mode is also suitable for extermination of large colonies in a field.

The mimetic egg containing the base material made of such a sustained-release material is also effective in the case that the active substance is slow-acting, and is particularly effective in the case that the active substance is not slow-acting.

The base material of the mimetic egg of the present invention may be made to contain, in addition to β-glucosidase, a salt thereof, a biological fragment of β-glucosidase or a β-glucosidase-related peptide, one or more kinds of other egg recognition pheromone. A kind or an amount of the other egg recognition pheromone can be appropriately selected depending on a kind of the targeted insect pests. When a insect pests is a termite, the base material of the mimetic egg of the present invention may be made to contain lysozyme, a salt thereof, a biological fragment of lysozyme or a lysozyme-related peptide. Lysozyme, a salt thereof, a biological fragment of lysozyme or a lysozyme-related peptide may be derived from any species of organisms, for example, may be derived from egg white lysozyme, a salt thereof, biological fragment thereof or a related peptide thereof. It is not necessary to use, as the egg recognition pheromone used in addition to β-glucosidase, a salt thereof, a biological fragment of β-glucosidase, or a β-glucosidase-related peptide used in the mimetic egg of the present invention, a highly purified product. The content of the egg recognition pheromone in the base material can be determined depending on various factors such as the kind, the characteristic, and the amount of the β-glucosidase to be used, the kind of the insect pests, the kind or the amount of the active substance, and the kind or the extent of the desired effect.

The lysozyme salt may be a salt with every substance that can form a salt, for example, a salt with an organic acid, a salt with an inorganic acid, a salt with an organic base, or a salt with an inorganic base. Moreover, for example, a β- or γ-carboxyl group of asparagine acid or glutamine acid constituting the lysozyme and a metal such as sodium or potassium may form a salt. Moreover, for example, a salt may be formed with a side chain of a basic amino acid constituting the lysozyme. In the present invention, a biological fragment of lysozyme or a lysozyme-related peptide may have a form of a salt. The biological fragment of lysozyme is a polypeptide or a peptide having a partial amino acid sequence of lysozyme and having an egg recognition activity similar to lysozyme. The lysozyme-related peptide is a protein, a polypeptide, or a peptide having a similar egg recognition activity to lysozyme and being different from lysozyme and the biological fragment of lysozyme. The lysozyme-related peptide may be derived from a natural source or may be a synthetic compound. The lysozyme-related peptide may have an amino acid sequence different from the natural lysozyme by a technique such as a site-directed mutagenesis method.

Moreover, for example, it is also preferable that the base material of the mimetic egg of the present invention contain a component extracted from the egg of the targeted insect pests. Whereby, higher egg conveyance effect can be obtained. The crude extract from the egg may be contained in the base material, or the purified extract may be contained in the base material. The content of the crude extract or purified product thereof in the base material can be determined depending on various factors such as the kind, the characteristic, and the amount of the β-glucosidase to be used, a salt thereof, a biological fragment of β-glucosidase or a β-glucosidase-related peptide, the kind of the insect pests, and the kind or the extent of the desired effect. Methods known in the art can be used for a method of extracting and purifying an effective ingredient from an egg.

Glycerol may also be contained in the base material in order to maintain or stabilize the activity of β-glucosidase, a salt thereof, a biological fragment thereof or a β-glucosidase-related peptide as egg recognition pheromone in the mimetic egg of the present invention, and to hold it on the surface of the base material. For the same purpose, cellulase, a salt thereof, a biological fragment thereof or a cellulase-related peptide may also be contained in the base material. Cellulase used in the present invention, a salt thereof, a biological fragment thereof or a cellulase-related peptide may be derived from any species of organisms, or a synthetic compound.

The cellulase salt may be a salt with every substance that can form a salt, for example, a salt with an organic acid, a salt with an inorganic acid, a salt with an organic base, or a salt with an inorganic base. Moreover, for example, a β- or γ-carboxyl group of asparagine acid or glutamine acid constituting the cellulase and a metal such as sodium or potassium may form a salt. Moreover, for example, a salt may be formed with a side chain of a basic amino acid constituting the cellulase. In the present invention, a biological fragment of cellulase or a cellulase-related peptide may have a form of a salt. The biological fragment of cellulase is a polypeptide or a peptide having a partial amino acid sequence of cellulase and having an activity and an action similar to cellulase. The cellulase-related peptide is a protein, a polypeptide or a peptide having an activity and an action similar to cellulase and being different from cellulase and the biological fragment of cellulase. The cellulase-related peptide may be derived from a natural source or may be a synthetic compound. The cellulase-related peptide may have an amino acid sequence different from the natural cellulase by a technique such as a site-directed mutagenesis method.

A highly purified glycerol or cellulase is not necessarily used. The content of glycerol or cellulase in the base material can be determined depending on various factors such as the kind, the characteristic, and the amount of the β-glucosidase to be used, the kind of the insect pests, the kind or the amount of the active substance, and the kind or the extent of the desired effect.

In another aspect, the present invention provides a method for exterminating insect pests, which includes providing the mimetic egg of the present invention to the insect pests. The insect pests exterminated or controlled by the method of the present invention may be any insect pests as long as it has an egg conveyance instinct and recognizes β-glucosidase, a salt thereof, a biological fragment thereof or a β-glucosidase-related peptide as egg recognition pheromone. Applying the mimetic egg of the present invention to a termite can induce egg conveyance and an egg protection behavior and can allow a termite to convey the mimetic egg into its egg mass in the nest. This not only allows he termite to convey the mimetic egg into breeding room in the nest but also can induce care behaviors such as licking the surface of the mimetic egg. It is possible to extremely efficiently exterminate insect pests by making the mimetic egg to contain an active ingredient such as an insecticidal active ingredient or a growth-inhibiting ingredient.

The insect pests to which the extermination method of the present invention is preferably applied is a termite. In the case of exterminating a termite, the mimetic egg of the present invention can be put on a part of an ant road or a nest material. Holes are opened on an ant road by a drill, and the mimetic egg of the present invention can be injected into them. The mimetic egg of the present invention can also be enveloped in a protective film such as cellophane to maintain durability in the field. In this case, an ingestion-promoting substance such as a wood extract liquid or a rotten wood extract liquid may be added to the protective film. It is also effective to use a monitoring station for the method for exterminating insect pests of the present invention.

Since, by using the mimetic egg of the present invention, an egg conveyance behavior of an insect can be easily induced and observed, the mimetic egg of the present invention is also suited as a tool for a biological study for learning and studying of a behavior and pheromone of an insect. Therefore, the present invention provides, in still another aspect, a tool for a biological study essentially including the mimetic egg of the present invention. The tool of the present invention may be the mimetic egg per se of the present invention, a combination of the mimetic egg and an appliance required for a test, for example, a test kit. Using the tool of the present invention, a behavior and pheromone of an insect can be studied, or social behaviors such as an egg conveyance behavior or a grooming behavior of an insect can be studied.

The present invention will be described more specifically and in detail by the following Examples, but the Examples are for exemplification only and they are not intended to limit the present invention.

EXAMPLE 1

Example 1

Preparation of Mimetic Egg and Confirmation of Egg Recognition Activity of β-Glucosidase Egg recognition activities of a termite egg extract, β-glucosidase, egg white lysozyme, cellulase, a mixture of egg white lysozyme and cellulase, a mixture of egg white lysozyme and β-glucosidase, a mixture of egg white lysozyme, β-glucosidase and cellulase, and an aqueous 50% glycerin solution as a control were investigated by using a *Reticulitermes speratus* worker (worker termites).

Each test sample was prepared as follows.

800 µL of ultrapure water was added to 400 mg of a *Reticulitermes speratus* egg in an Eppendorf tube, homogenized, and subjected to ultrasonic treatment for 5 minutes, and centrifugation was performed at 15,000 rpm for 30 minutes. The supernatant was lyophilized, and 5.0 mg of the lyophilized powder was dissolved in 100 µL of an aqueous 30% glycerin solution (termite egg extract). An almond-derived β-glucosidase (Product#: G0395-5KU, Lot#: 047K4037, SIGMA-ALDRICH) (1.0 mg) was dissolved in 10 µL of an aqueous 50% glycerin solution (β-glucosidase). A chicken egg white lysozyme (Product#: L7651-10G, Lot#: 056K16901, SIGMA-ALDRICH) was desalted using a dialysis membrane SnakeSkin (7000MWCO, Product#: 68700, PIERCE) and then 2.0 mg of the desalted chicken egg white lysozyme was dissolved in 10 µL of an aqueous 50% glycerin solution (egg white lysozyme). A *trichoderma* viridae-derived cellulase (Product#: C1794-5KU, Lot#: 074K1304, SIGMA-ALDRICH) (1.0 mg) was dissolved in 10 µL of an aqueous 50% glycerin solution (cellulase). An egg white lysozyme (2.0 mg) and 1.0 mg of cellulose were dissolved in 10 µL of an aqueous 50% glycerin solution (mixed solution of egg white lysozyme and cellulase). An egg white lysozyme (2.0 mg) and 1.0 mg of β-glucosidase were dissolved in 10 µL of an aqueous 50% glycerin solution (mixture of egg white lysozyme and β-glucosidase). An egg white lysozyme (2.0 mg), 1.0 mg of β-glucosidase and 1.0 mg of cellulose were dissolved in 10 µL of an aqueous 50% glycerin solution (mixture of egg white lysozyme, β-glucosidase and cellulase).

2.0 µL of each of the test samples was added to equal amounts of 100 glass beads having a diameter of 0.5 mm and blended well, whereby, the test sample was coated on the surface of the glass bead. The glass beads coated only with an aqueous 50% glycerin solution were used as a control.

Figure 2:
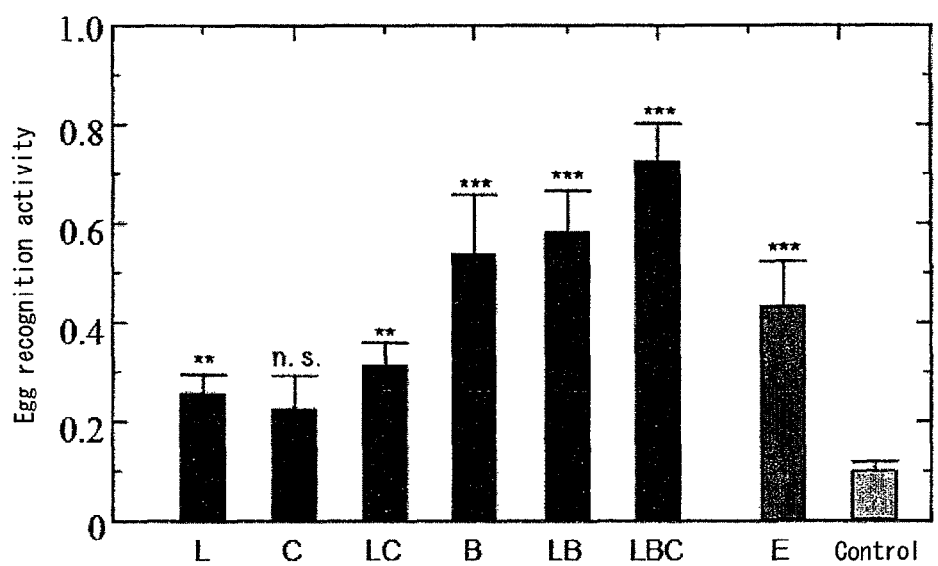
FIG. 2 shows results of investigation of an egg recognition activity (conveyance ratio) after 48 hours since initiation of a test. The abbreviations and symbols are the same as those of FIG. 1.

10 termite eggs and 20 mimetic eggs obtained by the above procedure were randomly put on a petri dish having a diameter of 30 mm, and 10 worker termites (workers) of *Reticulitermes speratus* were put therein, and the petri dish was allowed to stand in a constant temperature room of 25° C. After 24 hours and 48 hours since the beginning of the test, the conveyance ratio of the mimetic eggs into the egg mass was investigated (the experiment was performed by the same procedure for each of the test samples). Eight experiments were repeated for each test. The conveyance ratio was converted into arcsine root, and statistical comparison with the control was performed by a two-side T-test. The worker termites gathered the eggs scattered on the petri dish to form an egg mass and showed a conservation behavior. The conveyance ratio of the mimetic eggs coated with each of the test samples into the egg mass (after 24 hours) is shown in FIG. 1. The conveyance ratio of the mimetic eggs into the egg mass (after 48 hours) is shown in FIG. 2.

As a result of the addition of β-glucosidase, an egg recognition activity remarkably increased. Upon observation after 24 hours and 48 hours, as compared with the experiment of only in lysozyme and cellulose in which β-glucosidase is not added, the experiment in which β-glucosidase is added showed significantly high egg recognition activity ($P<0.001$, two-side T-test). In particular, the mimetic eggs containing β-glucosidase, lysozyme and cellulase showed a high conveyance activity.

Industrial Applicability

The present invention provides effective extermination and control of insect pests, particularly a termite, and can be utilized in the fields of production of insecticides, insect pests expelling industry, building industry and landscape industry. Furthermore, the present invention can also be utilized in the field of biological investigation.

The invention claimed is:

1. A mimetic egg comprising β-glucosidase or salt thereof as an egg recognition pheromone in its base material mimicking an egg of a termite, wherein the β-glucosidase is a β-glucosidase from almonds, cycads, a termite, a wood feeding cockroach, a snail, *Aspergillus oryzae*, yeast, an *Enterococcus* bacterium, or a *Bacillus* bacterium, and wherein the base material comprises a chicken egg white lysozyme or salt thereof, and a trichoderma viridae-derived cellulase or salt thereof.

2. The mimetic egg according to claim 1, wherein the base material further comprises an ingredient extracted from an egg of a termite.

3. The mimetic egg according to claim 1, wherein the base material further comprises glycerol.

4. A method for exterminating a termite, which comprises providing the mimetic egg according to claim 1 to a termite; and making the termite to convey the mimetic egg into its nest utilizing an egg conveyance behavior.

5. A tool for a biological study essentially comprising the mimetic egg according to claim 1.

* * * * *